United States Patent [19]

Cummings et al.

[11] Patent Number: 5,150,291
[45] Date of Patent: Sep. 22, 1992

[54] RESPIRATORY VENTILATION APPARATUS

[75] Inventors: Charles C. Cummings, Towson, Md.; Robert I. Prince, Gainesville, Fla.

[73] Assignee: Puritan-Bennett Corporation, Carlsbad, Calif.

[21] Appl. No.: 593,324

[22] Filed: Oct. 1, 1990

Related U.S. Application Data

[63] Continuation of Ser. No. 512,577, Apr. 20, 1990, abandoned, which is a continuation of Ser. No. 845,942, Mar. 31, 1986, abandoned.

[51] Int. Cl.⁵ .............................................. G06F 15/42
[52] U.S. Cl. ........................... 364/413.03; 128/204.24; 128/205.24
[58] Field of Search ................... 324/413.02, 413.03; 137/908; 128/204.23, 204.24, 205.24, 205.24, 205.19

[56] References Cited

U.S. PATENT DOCUMENTS

| | | | |
|---|---|---|---|
| 3,923,055 | 12/1975 | Hammacher | 128/204.23 |
| 4,141,354 | 2/1979 | Ismach | 128/204.26 |
| 4,155,356 | 5/1979 | Venegas | 128/204.23 |
| 4,182,366 | 6/1980 | Boehringer | 137/510 |
| 4,211,221 | 7/1980 | Schwanbom | 128/204.26 |
| 4,318,399 | 3/1982 | Berndtsson | 128/204.23 |
| 4,450,838 | 5/1984 | Miodownik | 128/696 |
| 4,461,293 | 7/1984 | Cher | 128/204.24 |
| 4,462,398 | 7/1984 | Durkan et al. | 128/204.24 |
| 4,463,756 | 8/1984 | Thuc | 128/204.24 |
| 4,506,666 | 3/1985 | Durkan | 128/204.24 |
| 4,538,604 | 9/1985 | Usry | 128/204.25 |
| 4,552,142 | 11/1985 | Hoffman et al. | 128/207.16 |
| 4,570,631 | 2/1986 | Durkan | 128/204.24 |
| 4,613,111 | 9/1986 | Paquet | 251/30.01 |
| 4,617,924 | 10/1986 | Heim | 128/204.25 |

OTHER PUBLICATIONS

Pinchak et al. "Beat Frequencies in High Frequency Positive Pressure Ventilation" *Critical Care Medicine*, vol. 12, No. 9 Sep. 1984.
Pinsky et al. "Hemodynamic Effects of Cardiac Cycle-Specific Increases in Intrathoracic Pressure" 1986.
Pinsky et al. "Cardiac Augmentation by Phasic High Intrathoracic Pressure Support In Man" *Chest*, vol. 84, No. 4, 1983.
Tyson et al. "The Mechanical Effects of High Frequency Ventilation of Cardiac Function in Intact Dogs" (Abstract) *Critical Care Medicine*, Mar. 1982.
Klain et al. "Circulatory Assist by High Frequency Ventilation" (Abstract) *Critical Care Medicine*, Apr. 1980.
Pinsky et al. "Hemodynamic Effect of Cardiac Specific Increases In Intrathoracic Pressure in Normo- and Hypovolemia" (Abstract) 1982 or 1983.
Dorinsky et al., "The Effects of PEEP on Cardiac Output", *Chest*, vol. 84, No. 2, 1983.

*Primary Examiner*—Gail O. Hayes
*Attorney, Agent, or Firm*—Fulwider, Patton, Lee & Utecht

[57] ABSTRACT

A gating system is provided for controlling a ventilator means, which, in turn, generates a positive pressure breath. The systems including a sensing means for sensing sequential heart beats of a patient, together with a computing means, which is connected to the sensing means, for computing a period between the sequential heart beats. In addition to the above, a valve means is connected electrically to the computing means and pneumatically to the ventilator means for controlling the ventilator means, with the valve means being positioned to cease positive pressure breaths in response to the computer period.

26 Claims, 1 Drawing Sheet

RESPIRATORY VENTILATION APPARATUS

This application is a continuation of application Ser. No. 07/512,577, filed Apr. 20, 1990, now abandoned, which is a continuation of application Ser. No. 06/845,942, filed Mar. 31, 1986, now abandoned.

BACKGROUND

When breathing normally, one's diaphragm is dropped to increase one's thoracic cavity, thus creating a negative pressure in the thoracic cavity, relative to atmospheric pressure. Air is driven by the atmospheric pressure into the negative-pressure thoracic cavity. Many patients, such as victims of accidents suffering from shock, trauma or heart attack, may require a respirator or ventilator to aid breathing. Prior respirators used intermittent, positive pressure breaths to increase the pressure within a patient's lungs until filled. Air is expelled passively by the natural stiffness of the lungs.

Such respirators drive a positive pressure breath into the lungs which are already at atmospheric pressure. The pressure in the lungs is increased above atmospheric pressure, contrary to normal occurrence, which inhibits the heart's ability to pump blood. During normal respiration, negative thoracic pressure is developed upon inspiration of air, which aids in filling the heart with blood. The resultant pressure gradient (the relatively positive pressure in the periphery and negative pressure in the thorax) helps to fill the heart as it opens, subsequent to the heart's squeezing or pumping motion. If however, the pressure in the thoracic chamber is increased, as with respirators, the amount of blood returning or entering the heart is decreased. The heart also must squeeze against a higher pressure. A lower cardiac output results.

The common technique for improving arterial oxygen tension is the use of Positive-End-Expiratory Pressure (PEEP), where a low level of positive pressure is maintained in the airway between positive pressure breaths. PEEP uses a standard switch. A pressure signal applied to the valve controls the high or low pressure states of the valve. The low PEEP state is generated when the valve is fully open. A partial closing of the valve creates high intrathoracic pressure between breaths, as some air from the tidal volume is not allowed to escape. However, at 10 centimeters of water pressure of PEEP, cardiac output drops significantly. Intravenous fluids are used to increase intravascular volume in an effort to minimize this fall in cardiac output. The patient may already have compromised cardiac function, minimizing or negating the advantages of the intravascular volume increase Additionally, patients requiring respirators typically lack adequate kidney function and cannot process the added fluids. If too much intravenous fluid is used, relative to the patient's ability (aided or not) to process the fluid, the fluid may enter the patient's lungs.

Positive inotropic agents are used to increase the squeeze of the heart to pump more blood. Obviously, the heart works harder than normal resulting in possible heart attacks or arrhythmias. Often, physicians will prescribe a combination of increased intravenous fluids and positive inotropic agents with PEEP.

Several investigators have evaluated the effect of cardiac cycle-specified, increases in thoracic pressure on cardiac output. They synchronized high frequency jet ventilation to various phases of the R-R interval Carlson and Pinsky found that the cardiac depressant effect of positive pressure ventilation is minimized if the positive pressure pulsations are synchronized with diastole. Otto and Tyson, however, found no significant changes in cardiac output while synchronizing positive pressure pulsations to various portions of the cardiac cycle.

Pinchak described the best frequency in high frequency jet ventilation. He also noticed rhythmic oscillations in pulmonary artery pressure (PAP) and also rhythmic changes in systemic blood pressure. A possible explanation for these oscillations is that the jet pulsations move in and out of synchrony with the heart rate. In evaluating his data it appears that when jet airway pressure peak occurred during early systole there was a high pulmonary artery pressure, and a low systemic blood pressure. While Pinchak does not comment on this, his recorded data show that pulmonary artery pressure was waxing and waning precisely opposite to the blood pressure. A plausible explanation is an increase in pulmonary artery pressure is simply a reflection of an increase in pulmonary vascular resistance which causes a decrement in left ventricular filling and thus decrease in systemic blood pressure secondary to a decrease in cardiac output. If the slight oscillations in the systemic blood pressure reflect oscillations in cardiac output, then Pinchak's study would support Pinsky and Carlson's work, suggesting that positive airway pressure is least detrimental during diastole.

It is an object of this invention to provide a computer gated system for controlling the pressure maintained in the airway of a patient between positive pressure breathes delivered by aventialor which operates in conjunction with a positive end-expiratory pressure valve mechanism.

Still another object of this invention to provide a computer-gated positive expiratory pressure system which is reliable and efficient in operation, economical to manufacture, and easy to maintain.

And even another object of this invention to provide a computer-gated pressure system as an adjunct to positive end-expiratory pressure systems.

And a further object of this invention to provide a computer-gated expiratory pressure system for controlling a breath of a patient.

SUMMARY OF THE INVENTION

The invention concerns a gating system for controlling the pressure maintained in the airway between positive pressure breaths delivered by a ventilator which operates in conjunction with a positive end-expiratory pressure (PEEP) valve. The system includes a sensing means for sensing sequential heart beats of a patient, a computing means, connected to the sensing means, for computing a period between the sequential heart betas, and a three-way valve connected electronically to the computing means and pneumatically to a valve means, for controlling the valve means. The three-way valve is controlled by the computing means so as to open and close the valve means, ceasing positive pressure delivered to the patient for an interval determined by the computer means in response to the sensing means. Control of the valve means is further accomplished through the use of a vacuum means and a positive pressure means which deliver positive or negative pressure, via the three-way valve, to the valve means and cause opening and closing of the valve means. Upon opening, the valve means allows the respiratory system to be in contact with the atmosphere, allowing a brief, precise drop in pressure. When closed, the valve means allows normal operation of the respirator opening in conjunction with the PEEP valve.

Thus, PEEP is removed for a variable time ratio immediately before a next heart beat. The PEEP valve is controlled by computer gating a 3-way valve to create pressure drops, allowing the heart to fill. Once the heart fills, PEEP is resumed without any detrimental effects. Respiration of the patient is coordinated with the patient's heart beat to maximize cardiac output. Additionally pressure can be replaced immediately after drop out in an effort to improve emptying of the heart.

DETAILED DESCRIPTION OF THE INVENTION

Figure 1:
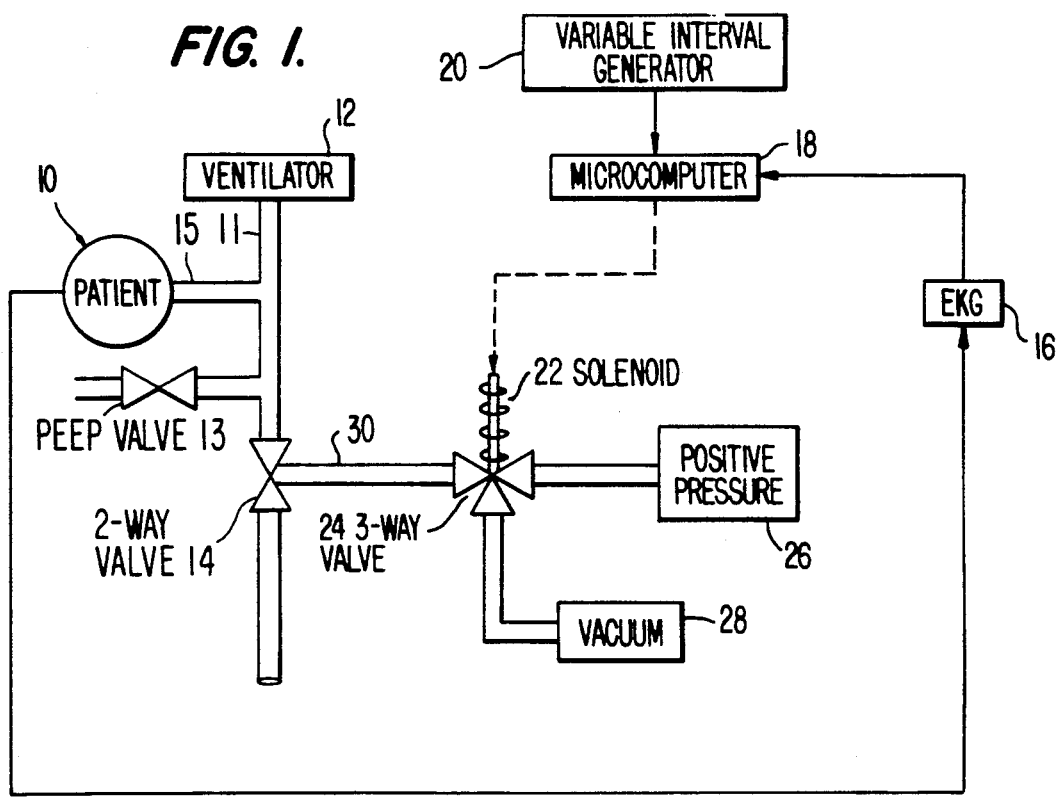
FIG. 1 is a schematic of the present invention in its environment with a patient.

The computer-gated, positive expiratory pressure system is shown in FIG. 1 in its environment, connected to a therapeutic device such as a PEEP ventilator system. A patient 10 is shown using a respirator or ventilator 12 via a standard expiratory ("peep" type computer controlled) valve 13. The PEEP valve 14 opens and closes to allow low and high pressures to the patient 10. In accordance with the present invention, the patient 10 is also connected to a cardiogram machine (EKG) 16. Successive heart beats are detected by the EKG 16 and a signal representing each beat is output to a microcomputer 18, the details of which are discussed regarding FIGS. 2 and 3. A variable interval is generated by generator 20 as a second input to the microcomputer 18, the value of the interval being set by the attending physician. The microcomputer 18 combines the variable interval signal from 20 and a value representing the period between successive heart beats from EKG 16 and generates a controlling output to a solenoid 22 of a 3-way valve 24. The 3-way valve 24 is connected by a first end to a positive pressure source 26. A second valve end is pneumatically connected to a low relative pressure 28, while a third end is connected to the computer controlled valve 14 through which the patient 10 received the positive pressure breaths.

Under normal operation of the ventilator 12, the PEEP valve 13 is operated to allow alternate low and high positive pressure breaths (approximately .4 psi) from the ventilator 12 to pass directly to the patient 10. However, in response to the output of microcomputer 18, the solenoid 22 is energized to yield at output 30, a negative pressure from the low relative pressure source 28. The negative pressure output at 30 opens the computer controlled valve 14. Because the computer controlled valve 14 is fully opened, a relatively low pressure (atmospheric or slightly above atmospheric pressure) is received by the patient 10 from the ventilator 12. The resultant relatively low pressure, in accordance with the present invention, occurs just prior to a predicted heart beat to ensure the heart, when filling, does not work against high pressures. PEEP systems per se too often generate high pressures when the heart beats, inhibiting heart filling and decreasing cardiac output.

Figure 2:
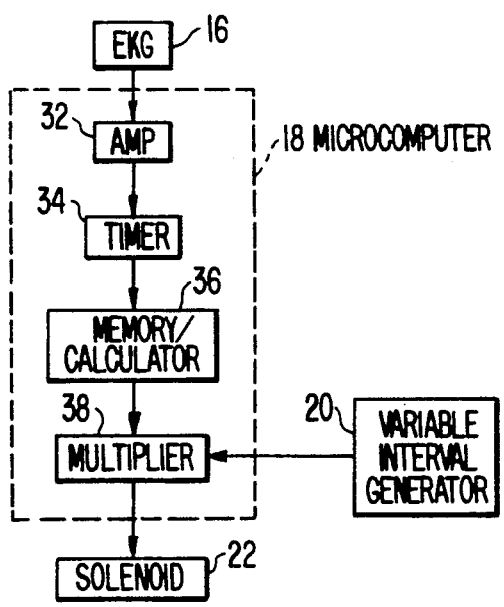
FIG. 2 is a block diagram of the FIG. 1 microcomputer contents, as connected to a 3-way valve.

In FIG. 2, the details of microcomputer 18 are evident. The output of EKG 16 is run through an operational amplifier 32 to a timer 34 which squares the amplified EKG signal to develop a series of electrical pulses corresponding to successive heart beats. The electrical pulses of timer 34 are received by memory/calculator 36 which determines a period representing the interval between successive heart beats) (R-R waves). This period is used to pred ct a next heart beat so a low pressure is delivered to the patient slightly before and during this next heart beat. The variable interval generator 20 is set by the attending physician between 15 and 400 microseconds, for instance, by typical analog controls. The variable interval signal from 20 and the period signal from calculator 36 are used to generate a product in multiplier 38 The resultant product (R-R wave period times variable interval) is used as a signal to energize the solenoid 22, to control 3-way valve 24.

In a normal state, 3-way valve 24 connects the positive pressure 26 to the output 30, putting computer controlled valve 14 in a closed position. Thus, the ventilator 12 can generate a high, positive pressure breath to the patient 10, and the PEEP valve 13 operating in normal fashion, causes a decrease in pressure to some positive-end expiratory pressure. However, assume the EKG 16 detects a heart beat each second. The EKG signal is amplified at 32, squared by timer 34, and the period of one second calculated in memory 36. If the variable interval generator is set by the physician for 0.8 second, multiplier 38 forms a product of the period and variable interval (1.0×0.8) equal to 0.8 seconds. Thus, 0.2 second before the next predicted, heart beat (0.8 second from the last heart beat) solenoid 22 is energized. The 3-way valve 24 now opens output 30 to the vacuum 28. Accordingly, a resultant negative pressure fully opens the computer controlled valve 14 and a low pressure reaches the patient. Should the heart rate vary, the difference between predicted and actual heart beats will be detected by the computing means and the pulse timing corrected. The time duration of the pulse to the solenoid is controlled by a second timer (not shown).

Figure 3:
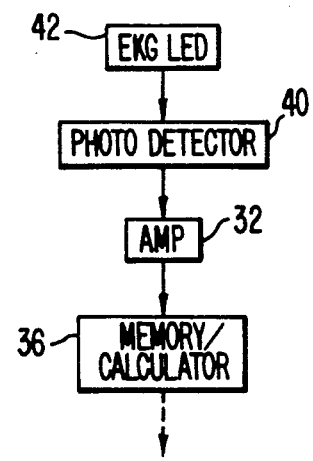
FIG. 3 reveals a second embodiment for detecting a heart beat interval.

FIG. 3 reveals a second embodiment for determining or sensing heart beats. A photodetector 40 is used to detect the blinking LED 42 which is typically part of a cardiogram machine. The photodetector 40, turning on and off with the flash of the LED 42, requires no timer or wave squarer, and thus is input directly to the amplifier 32 for subsequent processing in the manner of the FIG. 2 embodiment.

Other modifications are apparent to those skilled in the art which do not depart from the spirit of the present invention, the scope being defined by the appended claims. For instance, rather than use a microcomputer, a microprocessor (e.g. C 64 Commadore Computer) may be adapted and software developed to monitor and determine beat period, with a programmable variable interval for use by the physician.

As another example, the two-way valve 14 may be functionally combined in a single unit with part of the PEEP valve.

What is claimed is:

1. In a respiratory ventilation apparatus having a ventilator and a primary means for producing a pressure or volume supported breath cycle alternatingly providing a patient breathing pathway with a relatively high positive ventilation pressure and a relatively low positive ventilation pressure, the improvement comprising:

means for detecting heart beats in a plurality of cardiac cycles of said patient;

secondary means for producing said relatively low positive ventilation pressure in said patient breathing pathway commencing at a variable moment following a detected heart beat for a variable time interval during selected cardiac cycles; and means for determining said variable moment including means for determining a period of time between selected sequential heart beats of said patient, and means for multiplying a preselected multiplier value by said period of time between said selected sequential heart beats, said preselected multiplier value approximately corresponding to a computed fraction of said period of time between heart beats.

2. The apparatus of claim 1, wherein said secondary means for producing said relatively low positive pressure comprises control means for generating a control signal for a predetermined period of time commencing at said variable moment during selected cardiac cycles of said patient, a control valve means connected to said patient breathing pathway having an open position in which said control valve means induces said relatively low pressure in said breathing pathway, and means operatively connected to said control means responsive to said control signal for opening said control valve means.

3. The apparatus of claim 2, wherein said control means comprises microprocessor means.

4. The apparatus of claim 3, further including means for storing said preselected multiplier value.

5. The apparatus of claim 2, wherein said means for opening said control valve means comprises a pneumatic control valve.

6. The apparatus of claim 2, wherein said means for opening said control valve means comprises an electronic valve control.

7. The apparatus of claim 5, wherein said pnenumatical control valve includes an inlet connected to a source of vacuum, an outlet in communication with said control valve means, switch means electrically connected to said control means and operative to communicate vacuum from said vacuum source to thereby open said control valve means in response to said control signal.

8. The apparatus of claim 6, wherein said electronic control valve includes a connection to said control means operative to communicate an electrical signal from said control means to said electronic valve in response to said control signal.

9. The apparatus of claim 1, wherein said means for detecting heat beats comprises means for generating an electrical heart bet signal in response to said heart beat.

10. The apparatus of claim 9, further including means for amplifying said electrical heart beat signal.

11. The apparatus of claim 9, wherein said means for generating an electrical heart beat signal comprises an electrocardiograph.

12. The apparatus of claim 9, wherein said means for generating an electrical heart beat signal comprises means for generating a light signal in response to said heart beat, and photodetector means for detecting said light signal operative to generate said electrical heart beat signal responsive to said light signal.

13. A respiratory ventilation apparatus, comprising:
a ventilator having means for producing a pressure or volume supported breath cycle alternatingly providing a patient breathing pathway with a relatively high positive ventilation pressure and a relatively low positive ventilation pressure;

means for detecting heart beats of said patient;

control means for generating a control signal for a predetermined period of time commencing at a variable moment following selected patient heart beats, said control means including means for determining said variable moment including means for determining a period of time between sequential heart beats of said patient, and means for multiplying a computed multiplier value by said period of time between sequential heart beats to thereby generated a value representing said variable moment;

control value means connected to said patient breathing pathway having an open position in which said control valve induces said relatively low pressure in said breathing pathway; and means for opening said control valve means connected to said control means and responsive to said control signal.

14. The apparatus of claim 13, wherein said control means comprises microprocessor means.

15. The apparatus of claim 14, further including means for operator entry and storage of said preselected multiplier value.

16. In a respiratory ventilation apparatus having a ventilator and a primary means for producing a pressure or volume supported breath cycle alternatingly providing a patient breathing pathway with a relatively high positive ventilation pressure and a relatively low positive ventilation pressure, the improvement comprising:

means for detecting heart beats in a plurality of cardiac cycles of said patient, including means for generating an electrical heart beat signal in response to said heart beat, and amplifying means for squaring said electrical heart beat signal;

secondary means for producing said relatively low positive ventilation pressure in said patient breathing pathway commencing at a variable moment following a detected heart beat for a variable time interval during selected cardiac cycles; and means for determining said variable moment.

17. The apparatus of claim 16, wherein said secondary means for producing said relatively low positive pressure comprises control means for generating a control signal for a predetermined period of time commencing at said variable moment during selected cardiac cycles of said patient, a control valve means connected to said patient breathing pathway having an open position in which said control valve means induces said relatively low pressure in said breathing pathway, and means operatively connected to said control means responsive to said control signal for opening said control valve means.

18. The apparatus of claim 17, wherein said means for opening said control valve means comprises a pneumatic control valve.

19. The apparatus of claim 18, wherein said pneumatic control valve includes an inlet connected to a source of vacuum, an outlet in communication with said control valve means, switch means electrically connected to said control means and operative to communicate vacuum from said vacuum source to thereby open said control valve means in response to said control signal.

20. The apparatus of claim 17, wherein said means for opening said control valve means comprises an electronic valve control.

21. The apparatus of claim 20, wherein said electronic control valve includes a connection to said control means operative to communicate an electrical signal from said control means to said electronic valve in response to said control signal.

22. The apparatus of claim 16, wherein said means for determining said variable moment comprises means for determining a period of time between selected sequential heart beats of said patient, and means for multiplying a preselected multiplier value by said period of time between said selected sequential heart betas, said preselected multiplier value approximately corresponding to a computed fraction of said period of time between heart beats.

23. The apparatus of claim 17, wherein said control means comprises microprocessor means.

24. The apparatus of claim 22, further including means for storing said preselected multiplier value.

25. The apparatus of claim 16, wherein said means for generating an electrical heart beat signal comprises an electrocardiograph.

26. The apparatus of claim 16, wherein said means for generating an electrical heart beat signal comprises means for generating a light signal in response to said heart beat, and photodetector means for detecting said light signal operative to generate said electrical heart beat signal responsive to said light signal.

* * * * *